United States Patent [19]

Hasse et al.

[11] Patent Number: 4,685,915
[45] Date of Patent: Aug. 11, 1987

[54] DISPOSABLE DIAPER HAVING DENSITY AND BASIS WEIGHT PROFILED ABSORBENT CORE

[75] Inventors: Margaret H. Hasse, Wyoming; Mark J. Steinhardt, Loveland, both of Ohio

[73] Assignee: The Procter & Gamble Company, Cincinnati, Ohio

[21] Appl. No.: 597,619

[22] Filed: Apr. 6, 1984

[51] Int. Cl.$^4$ .............................................. A61F 13/16
[52] U.S. Cl. ............................... 604/378; 604/385 R
[58] Field of Search ............... 604/368, 369, 364, 365, 604/358, 380, 378, 379, 385.1

[56] References Cited

U.S. PATENT DOCUMENTS

| | | |
|---|---|---|
| Re. 29,789 | 10/1978 | Kolbach . |
| 3,592,194 | 7/1971 | Duncan . |
| 3,670,731 | 6/1972 | Harmon ............................. 604/364 |
| 3,766,922 | 10/1973 | Krusko . |
| 3,860,002 | 1/1975 | Kolbach ............................ 604/380 |
| 3,860,003 | 1/1975 | Buell . |
| 4,027,672 | 6/1977 | Karami . |
| 4,213,459 | 7/1980 | Sigl et al. . |
| 4,336,803 | 6/1982 | Repke . |
| 4,356,229 | 10/1982 | Brodnyan ........................... 604/365 |
| 4,381,782 | 5/1983 | Mazurak et al. .................... 604/369 |
| 4,388,056 | 6/1983 | Lee et al. .......................... 425/83.1 |
| 4,415,388 | 11/1983 | Korpman ........................... 604/369 |
| 4,429,001 | 1/1984 | Kolpin et al. . |
| 4,585,448 | 4/1986 | Enloe ................................ 604/378 |
| 4,610,678 | 9/1986 | Weisman et al. .................. 604/368 |

Primary Examiner—John D. Yasko
Attorney, Agent, or Firm—Steven W. Miller; Thomas J. Slone; Richard C. Witte

[57] ABSTRACT

A disposable diaper wherein a central portion of its absorbent core has a higher density and higher basis weight per unit area than longitudinally spaced end portions of the absorbent core. Such absorbent cores may comprise a mixture of hydrophilic fibers and discrete particles of a highly absorbent material such as, for example, hydrogel material.

19 Claims, 23 Drawing Figures

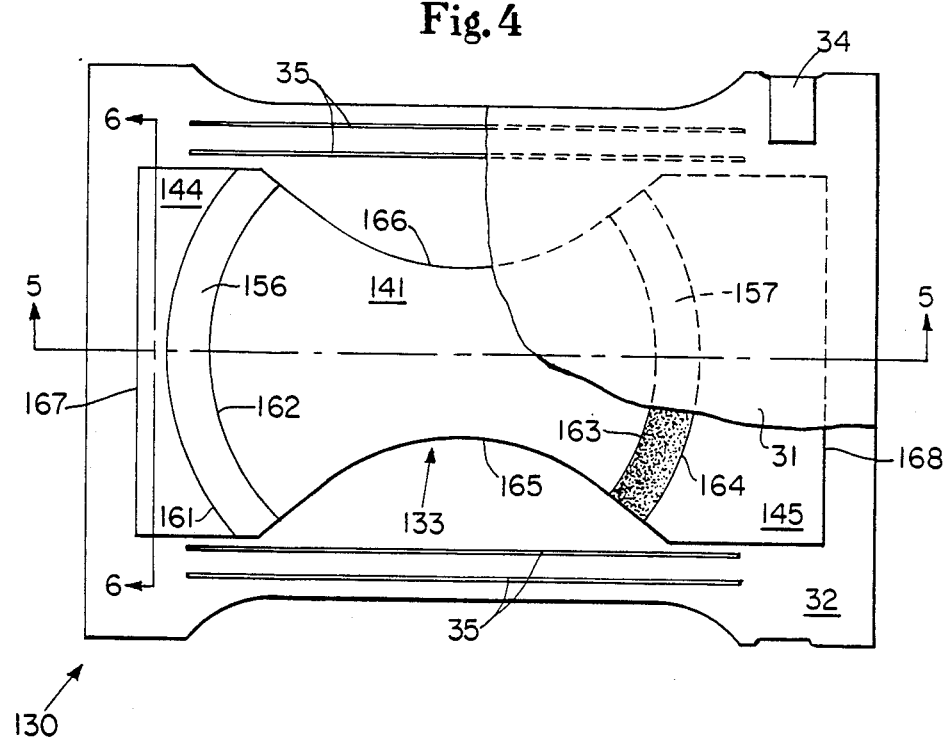
Fig. 4
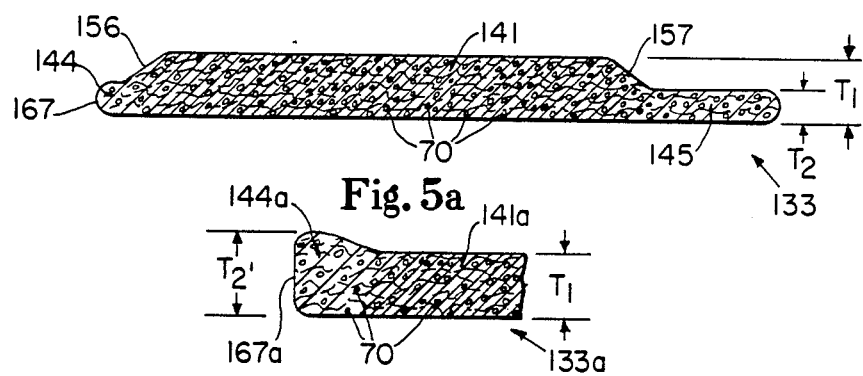
Fig. 5
Fig. 5a
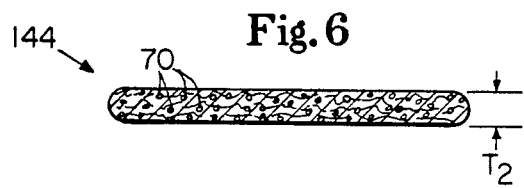
Fig. 6

DISPOSABLE DIAPER HAVING DENSITY AND BASIS WEIGHT PROFILED ABSORBENT CORE

TECHNICAL FIELD

This invention pertains to disposable absorbent products such as disposable diapers, and disposable briefs for incontinents. More specifically, this invention pertains to such products which have absorbent cores comprising hydrophilic fibers, or mixtures of hydrophilic fibers with discrete particles of highly absorbent materials such as, for example, water-insoluble hydrogels; and wherein the absorbent cores have central portions which are more dense and have higher basis weight per unit area than end portions of the core. As used herein, "highly absorbent materials" means materials which have the property to absorb water up to ten (10) or more times their own weights. Generally speaking such material will be present in particulate form in large enough particle sizes to not readily sift out of the fibrous matrix of the disposable diaper cores of interest, yet small enough particles to enable them to absorb effectively (e.g., sufficiently small to not have their potential absorbency substantially vitiated by gel blocking or analogous phenomena) and small enough that the diaper cores do not feel gritty.

BACKGROUND

A disposable diaper construction wherein the absorbent core has a thin dense central portion and thick, low density end portions is disclosed in U.S. Pat. No. 3,592,194 which issued July 13, 1971 to Robert C. Duncan; and a Disposable Diaper with Localized Area of Increased Density is disclosed in U.S. Pat. No. 4,213,459 which issued July 22, 1980 to Wayne C. Sigl et al., and which shows constructions having dense core areas which extend from the center of the crotch region to the rear edge of the core but which dense areas do not extend to the side edges of the core. An Apparatus For Continuously Making An Air-Laid Fibrous Web Having Patterned Basis Weight Distribution is disclosed in U.S. Pat. No. 4,388,056 which issued June 14, 1983 to Frankie B. Lee and Orin Jobes, Jr. Absorbent cores having patterned densification, and apparatus for making such cores are disclosed in U.S. Pat No. 4,027,672 which issued June 7, 1977 to Hamzeh Karami. Disposable diapers having profiled thicknesses, and compressed channels are disclosed in U.S. Pat. Nos. 3,766,922 which issued Oct. 23, 1973 to Evelyn H. Krusko, and Re. 29,789 which was reissued Oct. 2, 1978 to Charles G. Kolbach. Disposable diapers having elasticized contractable side portions and a variety of core shapes are shown in U.S. Pat. No. 3,860,003 which issued Jan. 14, 1975 to Kenneth Barclay Buell. Additionally, U.S. Pat. No. 4,335,803 which issued June 29, 1982 to Virginia L. Repke discloses disposable diapers having a variety of plan-view shaped cores which may have densified longitudinal lines for improved capillarity, and which have elasticized longitudinal edge portions. Furthermore, U.S. Pat. No. 4,429,001 which issued Jan. 31, 1984 to Barbara E. Kolpin et al. discloses an exemplary Sheet Product Containing Sorbent Particulate Material, and delineates a representative selection of additional patents which also disclose absorbent structures having particles of highly absorbent material dispersed in them.

DISCLOSURE OF THE INVENTION

A disposable diaper is provided which comprises a liquid pervious topsheet, a liquid impervious backsheet, and an absorbent core disposed between the topsheet and the backsheet. The absorbent core of the disposable diaper comprises two longitudinally spaced end portions and a central portion disposed therebetween. The absorbent core comprises absorbent material such as cellulosic fibers which are so disposed that the central portion has a greater average density per unit area and a greater average basis weight per unit area than each of the end portions. In accordance with one aspect of the invention, the ratio of the average density of the central portion to the average density of each of the end portions is about 2:1 or greater; and, more preferably, 2.5:1 or greater. The central portion is also preferably substantially uniformly dense and of uniform basis weight throughout its extent. In accordance with another aspect of the invention, the core comprises a mixture of hydrophilic fibers and discrete particles of a highly absorbent particulate material such as hydrogel particulate material, and the mixture has a fiber-to-particulate weight ratio of from about 70:30 to about 98:2; and, more preferably, from about 75:25 to about 90:10. In various other aspects of the invention: the fibers and the particulate of highly absorbent material are preferably uniformly dispersed; such particulate may be water-insoluble and may be disposed primarily or only in the central portion of the absorbent core; the absorbent cores may be configured to have laterally spaced ear regions which coact with either or both end portions to form a foldable waistband assemblage at one or both ends of the absorbent core; such waistbands may be of uniform density, or have thin, dense ear regions to facilitate folding and packaging, and to reduce bulk in the area of overlapping ear regions when worn by a user. In yet another aspect of the invention, the dense, high basis weight central portion of the absorbent core is spaced from the lateral side edges of the core by leg cuff portions of the core which are of lesser basis weight and density than the central portion; preferably about the same density and basis weight as the end portions of the core. In still other aspects of the invention, the central portions are more highly bonded internally and therefore are less resilient than the end portions of the absorbent core; and the various portions of the core are preferably demarked from each other by sufficiently abrupt thickness changes that the cores have terraced characters.

BRIEF DESCRIPTION OF THE DRAWINGS

While the specification concludes with claims which particularly point out and distinctly claim the subject matter regarded as forming the present invention, it is believed the invention will be better understood from the following description taken in conjunction with the accompanying drawings in which:

FIG. 4 is a plan view of an alternate disposable diaper embodiment of the present invention.

FIG. 5 is a longitudinal sectional view of the absorbent core of the disposable diaper of FIG. 4, and taken along sectional line 5—5 thereof.

FIG. 5a is a fragmentary longitudinal view similar to FIG. 5 but which shows the absorbent core of an embodiment of the invention wherein a low density front end portion is thicker than the adjacent central portion of the core.

FIG. 6 is a transverse sectional view of the core of the disposable diaper of FIG. 4, and taken along sectional line 6—6 thereof which extends through the front end portion of the disposable diaper.

DETAILED DESCRIPTION OF THE INVENTION

Figure 1:
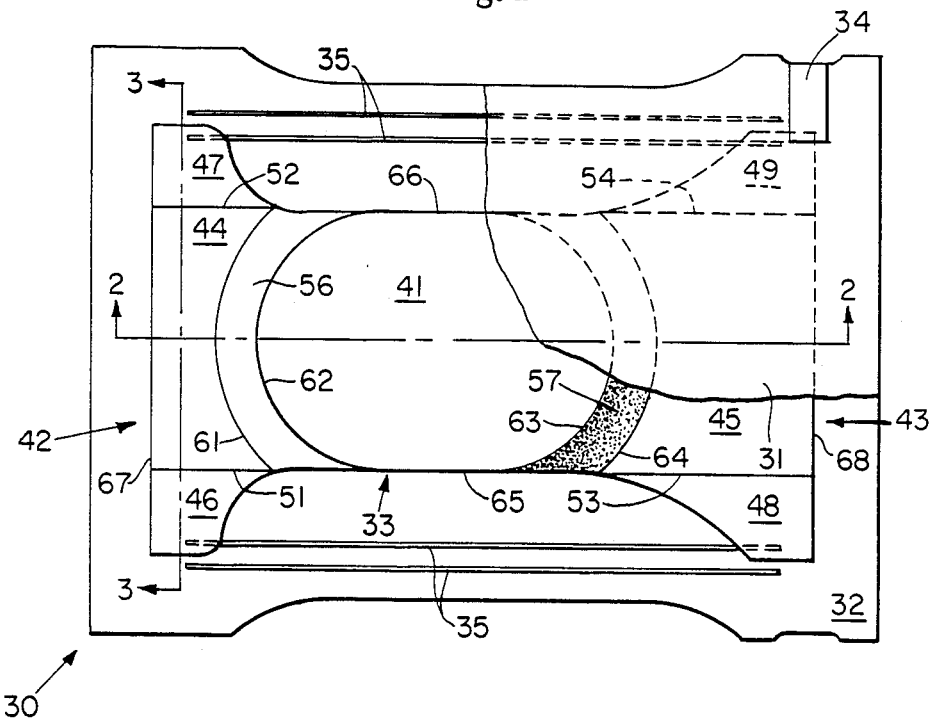
FIG. 1 is a plan view of a disposable diaper embodiment of the present invention wherein most of the topsheet has been torn away to more clearly show the underlying absorbent core of the diaper.

A disposable diaper 30 which is an exemplary embodiment of the present invention is shown in plan view in FIG. 1 to comprise a topsheet 31, a backsheet 32, an absorbent core 33, tape fasteners 34 only one of which is shown in FIG. 1 to be on a back corner of the diaper, and plural strands of elastic 35 which are affixed to the inwardly facing surface of backsheet 32 as by adhesive. The absorbent core 33 as shown in FIG. 1 comprises a central portion 41, and two waistband assemblages 42 and 43 which, in turn, comprise medial regions 44 and 45, respectively, and ear regions 46, 47, 48 and 49. Ear regions 46 and 47 are demarked from medial region 44 by edges designated 51 and 52, respectively, and ear regions 48 and 49 are demarked from medial region 45 by edges 53 and 54, respectively. Medial regions 44 and 45 are alternatively designated end portions 44 and 45 of the absorbent core 33. Additionally, absorbent core 33 comprises two basis weight/density transition zones 56 and 57 which are bounded in the plan view by arcuate lines 61, 62, 63 and 64, and by segments of the side edges 65 and 66 of absorbent core 33. Also, the end edges of the absorbent core 33 are designated end edges 67 and 68.

Figure 7:
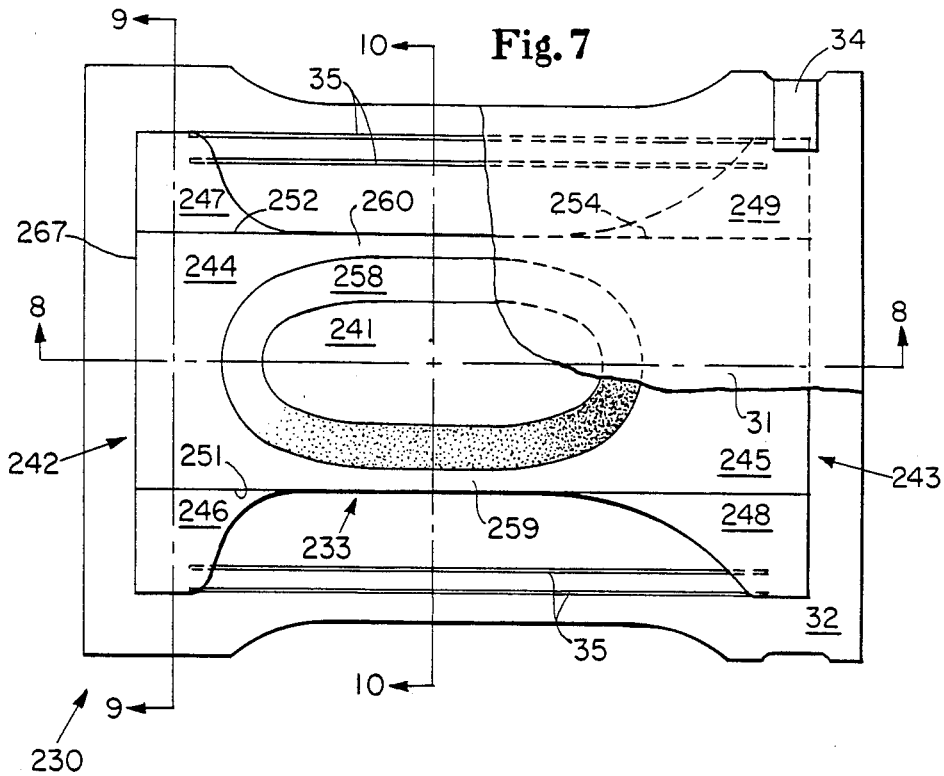
FIG. 7 is a plan view similar to FIGS. 1 and 4 which shows another alternate disposable diaper embodiment of the present invention.
Figure 8:
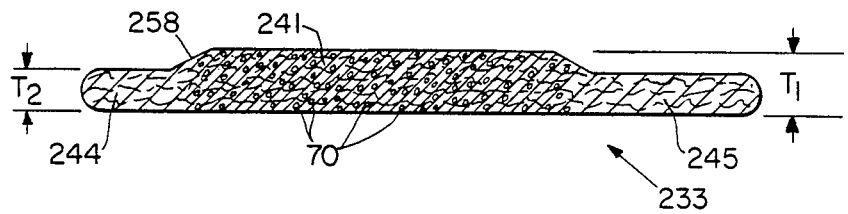
FIGS. 8, 9 and 10 are section views of only the core of the disposable diaper of FIG. 7, and taken along sectional line 8—8, 9—9, and 10—10 thereof, respectively.
Figure 9:
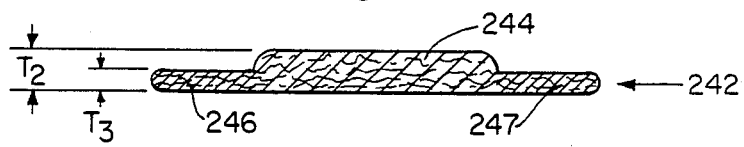
Figure 10:
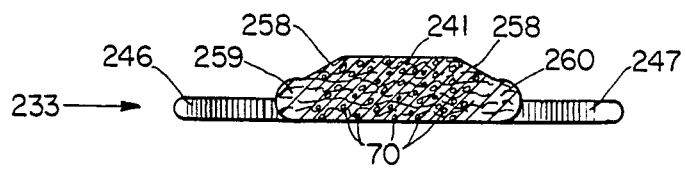

In the remaining views, features and elements which are substantially identical are identified throughout the views by the same designations; and, features and elements which generally are equivalent to those of disposable diaper 30 are identified by the same designators along with a hundreds digit. For example, alternate diapers shown in FIGS. 4 and 7 are designated 130, and 230, respectively; and absorbent cores thereof are designated 133 and 134, respectively. On the other hand, the topsheets, backsheets, and tape fasteners of disposable diapers 30, 130, and 230 are designated 31, 32, and 34, respectively, for each.

Figure 2:
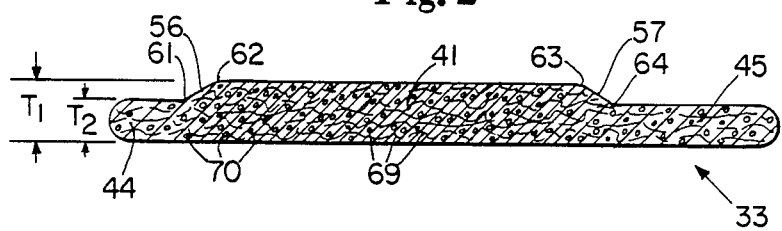
FIG. 2 is a longitudinal sectional view of only the absorbent core of the disposable diaper of FIG. 1, and taken along the medial sectional line 2—2 thereof.

Referring now to FIG. 2, a longitudinal sectional view of only the absorbent core 33 of diaper 30, FIG. 1, the central portion 41 of the absorbent core 33 is shown to be of uniform thickness $T_1$; of greater thickness than the thickness $T_2$ of end portions 44 and 45; and substantially more dense than end portions 44 and 45. Additionally, FIG. 2 depicts the core as being composed of fibrous material 69—preferably air laid, predominantly cellulosic fibrous material—having discrete particles 70 of a highly absorbent material dispersed throughout its extent.

Figure 3:
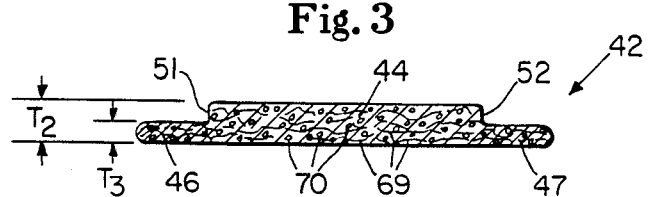
FIG. 3 is a transverse sectional view of only the absorbent core of the disposable diaper of FIG. 1, and taken along sectional line 3—3 thereof which extends through the front waistband assemblage of the disposable diaper.

FIG. 3, a transverse sectional view through the front waistband assemblage 42 of the absorbent core 33 of diaper 30, FIG. 1, shows the ear regions 46 and 47 to have a thickness $T_3$ which is substantially thinner than the thickness $T_2$ of medial region 44, and to be substantially more dense than the medial region 44. Such waistband assemblages may be made to have substantially uniform basis weight per unit area, and by then calendering the ear regions to effect the desired degrees of thickness reduction/densification. Such thin ear regions are particularly beneficial for reducing the bulk of the diaper in the side regions of users; particularly so if they are overlapped such as by having a front ear region disposed in overlapping relation with a rear ear region.

Briefly, referring to the exemplary disposable diaper 30, FIGS. 1 through 3, inclusive, the present invention provides a disposable diaper having an absorbent core 33 comprising a central portion 41 disposed intermediate longitudinally spaced end portions 44 and 45, and in which the central portion has both higher density and higher basis weight per unit area than the end portions: preferably having a ratio of the density of the central portion to the density of each of the end portions which is about equal to or greater than 2:1; and more preferably about 2—.5:1 or greater. Also, the central portion is preferably uniformly dense, and has substantially uniform thickness. Additionally, such cores preferably comprise a mixture of hydrophilic fibers 60 and discrete particles 70 of highly absorbent material such as, for example, a water-insoluble hydrogel wherein the weight ratio of the fibers to the absorbent particulate is from about 70:30 to about 98:2; and more preferably from about 75:25 to about 90:10. Moreover, preferably, only the central portion of the core has such highly absorbent particulate material dispersed in it; and, preferably, uniformly dispersed therein although it is not intended to thereby limit the present invention to constructions comprising uniformly disposed particulate absorbent material. Such diaper cores are so constructed that the lower density end portions stay dry due to the preferential capillarity of the central portion except when highly loaded: i.e., loaded with sufficient urine to sufficiently load the pores of the central portion that the excess urine will migrate into the lower density (large pored) end portions despite the fact such migration is opposite to the preferential capillarity of the structure. Thus, since the end portions preferably stay dry—i.e., their absorbency capacity not generally being utilized—they may be made to have very low basis weight to help hold down the cost of such diapers. Generally speaking, the particles of absorbent material dispersed throughout the fibrous matrix of the central portion of the core offset the potential absorbency capacity of the fibrous component thereof which is lost when it is compacted to give it its high density, preferential capillarity properties.

An exemplary disposable diaper 33, FIG. 1 was constructed in which the backsheet 32 is a matte-finish polyethylene film having a nominal thickness of about one mil (about 0.0254 mm); the topsheet 31 is a nonwoven, hydrophobic polypropylene having a nominal thickness of about three to five mils (about 0.056 mm to about 0.127 mm); an airlaid absorbent core 33 having a total weight of about thirty-one (31) grams; and weight ratio of fibers to hydrogel particles of about 85:15. The hydrogel particles were starch-grafted polyacrylate (e.g., Sanwet IM-1000 made by Sanyo Chemical Industries, Japan), and had a particulate size range of from about fifty (50) to about nine hundred (900) microns. Additionally, this diaper comprises strands 35 of elastic having nominal unstretched thickness and width of about 0.2 and 2.4 mm, respectively, which had been stretched about one-hundred-twenty-five percent (125) prior to being adhesively secured to the backsheet, and prior to adhesively securing the topsheet to the backsheet whereby the longitudinal side edges of the topsheet/backsheet composite in the leg cuff regions of the diaper have nominal extensions (i.e., their available stretch as a percent of their elastically contracted length) of about forty-five percent or greater. Additionally, the core 33 is preferably enveloped with a low basis weight tissue paper (not shown) to provide structural integrity. A particular size of this exemplary disposable diaper was sized and configured to accommodate an exemplary embodiment of core 33 which was constructed to be: approximately five-and-one-quarters inches (about 13.3 cm) wide across its central portion 41 (i.e., its crotch region); about eight-and-one-half inches (about 21.6 cm) wide across its waistband assemblages 42 and 43; about fifteen-and-one-quarter inches (about 38.7 cm) long; and to have basis weights in its central portion 41, end portions 44 and 45, and ear regions 46 through 49 of 0.07, 0.03, and 0.03 grams per square centimeter of surface area, respectively; and to have densities in its central portion 41, end portions 44 and 45, and ear regions 46 through 49 of about 0.18, 0.09, and 0.18 grams per cubic centimeter, respectively. Additionally, the core was configured and calendered so that the ear regions could be folded to overlay adjacent portions of their associated medial regions to form a generally rectangular shape, folded diaper albeit the strands of elastic pull the ends in somewhat. Preferably, for such folded diapers, $T_1$ will equal $T_2$ plus $T_3$ so that the folded diaper is uniformly thick. This is beneficial for packaging efficiency.

Such a core is preferably made by airlaying a thickness profiled core-perform of substantially uniform density; and then by calendering the core-preform in a fixed-gap calender wherein at least one calender roll has a stepped configuration to effect calendering the ear regions through a thinner gap than the gap through which the remainder of the core passes. Additionally, in embodiments comprising mixtures of fibers and absorbent particulate material, the particulate matter is preferably added to an air entrained stream of fibers prior to their deposition to form the core-preforms to effect uniform distribution of the particulate matter throughout the preform: or, more preferably, added in such a way as to be deposited in only the central portions of the core-preforms.

Referring now to absorbent particulate matter which may be included in embodiments of the present invention, hydrogel materials are very effective. By "hydrogel" as used herein is meant an inorganic or organic compound capable of absorbing aqueous fluids and retaining them under moderate prssures. For good results, the hydrogels should be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinly morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975, the disclosures of which are incorporated herein by reference. Particularly preferred polymers for use herein are hydrolyzed acrylonitrile grafted starch, acrylic acid grafted starch, polyacrylates, and isobutylene maleic anhydride copolymers, or mixtures thereof.

For the purpose of utilizing hydrogels in the present invention, it is essential that relatively dry hydrogel particles be used. Also, neither the fibers, the particles nor the mixture of fibers and particles should be exposed to water in its liquid form, or another solvent, at any time during this process or subsequent thereto. When wet hydrogel particles are used, the fibers tend to become entangled and/or bonded with the particles which result in undesirable stiffness of the absorbent structure. Additionally, wet hydrogel particles would obviously have less absorbency efficacy in the product inasmuch as their potential absorbency would already be diminished.

As used herein, "dry" does not mean "absolutely water-free". For example, under normal storage and handling conditions, hydrogel particles take up some moisture. The hydrophilic fibers also take up some moisture during storage. Furthermore, it may be desirable to use humidified air for air transport of the fibers and the hydrogel particles, to avoid dusting. Under such process conditions, the hydrogel particles and the fibers will take up even more moisture, but such should be limited so that it does not unduly affect the practice of the present invention.

Referring now to FIG. 4,, an alternate exemplary disposable diaper 130 is shown which differs from disposable diaper 30 in these respects: core 133 of diaper 130 has a longer central portion 141 than central portion 41 of core 33, and the side edges 165 and 166 of central portion 141 are convex as compared to the straight side edges 65 and 66 of core 33; end regions 144 and 145 of core 133 extend the full widths of the waistband portions of core 133, and core 133 has no ear regions comparable to the ear regions 46 through 49 of core 33.

As shown in FIG. 5, core 133 of disposable diaper 130, FIG. 4, has a terraced character by virtue of the thickness $T_1$ of central portion 141 being substantially greater than the thickness $T_2$ of the end portions 144 and 145, and by virtue of the relatively steep slopes of the basis weight/density transition zones 156 and 157. FIG. 6 shows the end portion 144 to be substantially uniformly thick an dense throughout, which is also preferably the case with end portion 145.

FIG. 5a shows a fragmentary longitudinal sectional view of a variant of disposable diaper core 133 which is designated 133a. FIG. 5a shows core 133a to have a front waistband edge 167a having a thickness $T_2$, as compared to the thin front waistband edge 167 of core 133, FIG. 5, having a thickness of $T_2$. Indeed end portion 144a is thicker and less dense than central portion 141a, albeit end portion 144a is of substantially lesser average basis weight per unit area than central portion 141a.

Briefly, depending on the propensity of the constituents of the core to become bonded to different extents when calendered to different degrees, a core preform as described hereinbefore which has a thicker and heavier basis weight central portion than its end portions may be selectively calendered to precipitate either thin end portion embodiments as represented by core 133, FIG. 5, or thick end portion embodiments as represented by core 133a, FIG. 5a. In embodiments comprising materials which hydrogen bond under pressure, moisture content of the core constituents may be controlled to precipitate the desired profile upon calendering. In general, relatively low moisture levels would enable precipitating the FIG. 5 type profile upon uniformly calendering the above described preform through a fixed-gap; and, relatively higher moisture levels would enable precipitating the FIG. 5a type profile.

Turning now to FIGS. 7 through 10, an additional alternate exemplary disposable diaper 230 which is an embodiment of the present invention is shown to be different from disposable diaper 30, FIGS. 1 through 3, by virtue of its central portion 241 being an island of high density, and high basis weight which is isolated from the edges of the core by: the combination of the end portions 244 and 245, and portions 259 and 260 which are hereby denominated leg cuff portions 259 and 260 of core 233; and by the race-track shaped portion 258 which is hereby denominated the basis weight/density transition zone 258 of core 233. Additionally, particulate absorbent material 70 is disposed only in the central portion 241 of core 233 to illustrate selective disposition thereof. However, it is not intended to thereby limit the present invention to such selectively disposed absorbent particulate material, or to limit the utility of such selective deposition of absorbent particulate matter to only cores of the configuration of core 233. In use, disposable diapers comprising such cores having high density/high basis weight island-shape central portions which are isolated from all of the core edges by portions having lower density and lower basis weight, tend to retain urine in the dense central portions and to remain dry or drier along all of its edges due to the preferential capillarity of the dense portion. This, of course, helps to obviate leakage around the edges of such diapers.

Additional alternate absorbent cores which are configured and constructed in accordance with the present invention are designated 333, 433, 533, 633, and 733 in FIGS. 11, 14, 17, 21 and 22, respectively. Broadly speaking: cores 333, 433 and 533 are rectilinear l-shape counterparts of the generally curvalinear-shape cores 33 (FIG. 1), 133 (FIG. 4), and 233 (FIG. 7), respectively. Additionally, core 33 is shown in FIG. 2 to have thinner and less dense end portions 344 and 345 (thickness $T_2$) relative to central portion 341 (thickness $T_1$); and, in FIG. 3, to have ear regions 346 and 347 which are more dense and thinner (thickness $T_3$) than end portion 344 (thickness $T_2$). Preferably, $T_1$, $T_2$ and $T_3$ are so related that $T_1$ is equal to the sum of $T_2$ and $T_3$ to enable efficient folding (of the ear regions over the central portions) and packaging as described hereinbefore. Also, albeit end portions 344 and 345 are shown to be equally thick and dense, it is not intended to thereby limit the invention; and, albeit it is preferably that end portions and ear regions have the same basis weight for, among other reasons, simplicity of manufacturing, it is also not intended to thereby limit the present invention.

Figure 11:
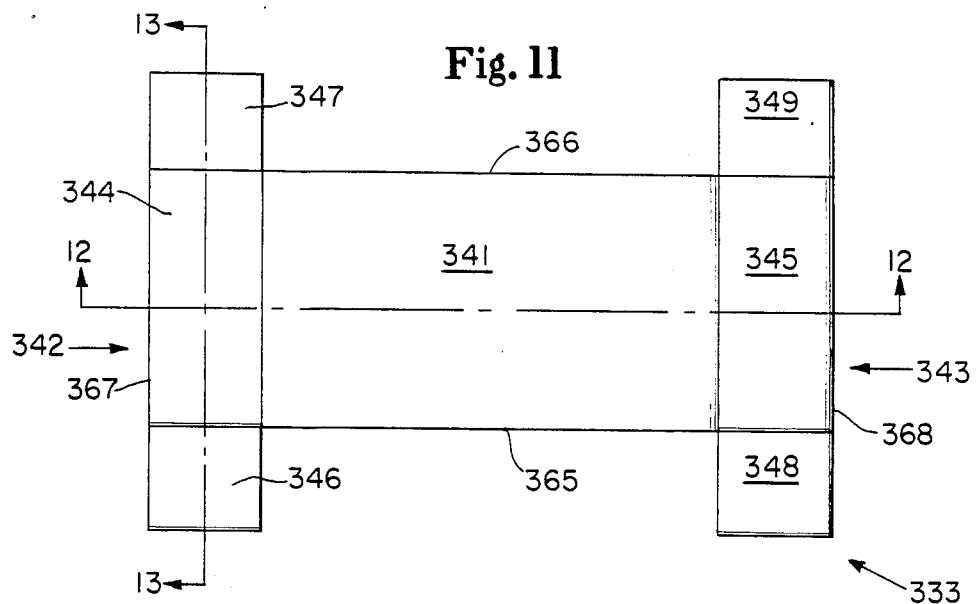
FIG. 11 is a plan view of a rectilinear absorbent core which is configured in accordance with the present invention to be l-shaped, and to have transversely spaced pairs of ear regions which are thinner and more dense than the end portions of the core.
Figure 12:
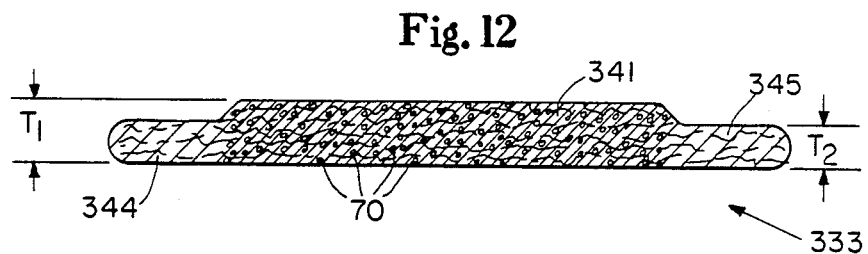
FIGS. 12 and 13 are sectional views taken along sectional lines 12—12 and 13—13, respectively, of FIG. 11.
Figure 13:
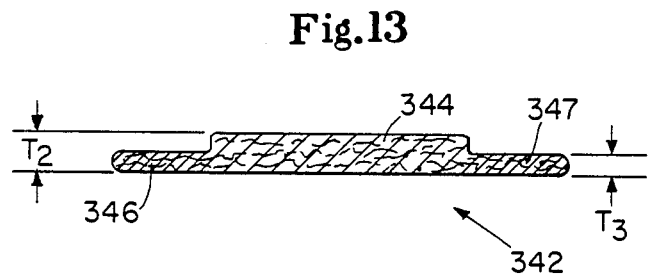
Figure 14:
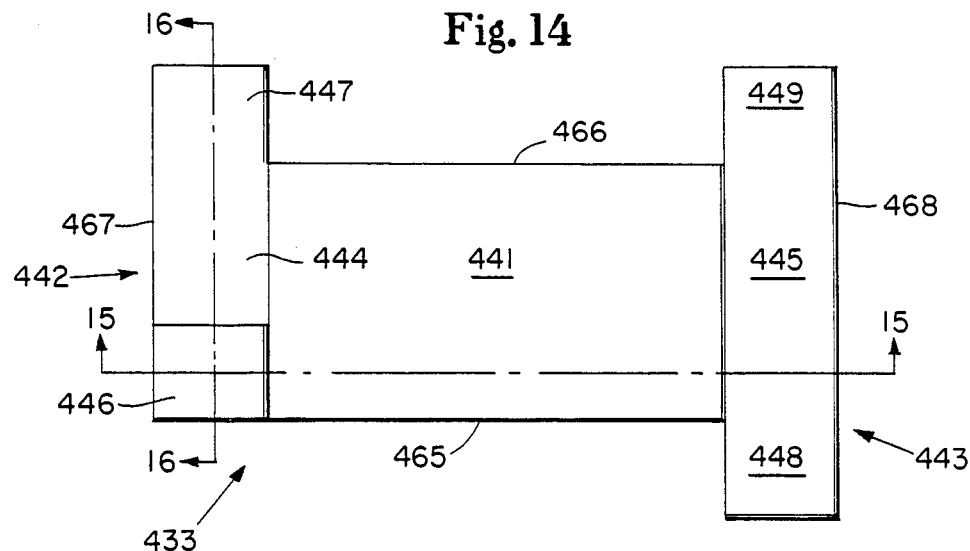
FIG. 14 is a plan view of an alternate embodiment, rectilinear l-shape absorbent core which is similar to that shown in FIG. 11 but for the waistband regions of the FIG. 14 embodiment being substantially uniformly dense and thick.
Figure 15:
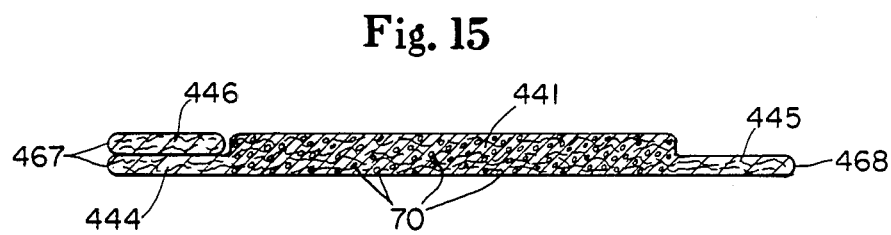
FIGS. 15 and 16 are sectional views taken along sectional lines 15—15 and 16—16, respectively, of FIG. 14.
Figure 16:
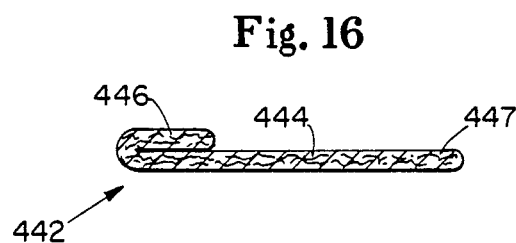
Figure 17:
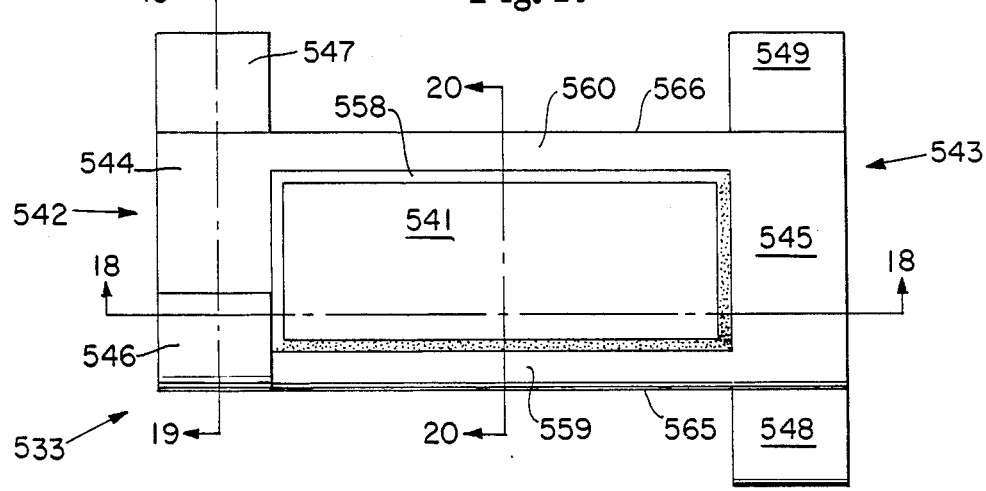
FIG. 17 is a plan view of another alternate embodiment, rectilinier l-shape absorbent core which is similar to the core shown in FIG. 11 except its dense central portion is isolated from all of the edges of the core by low density portions of the core.
Figure 18:
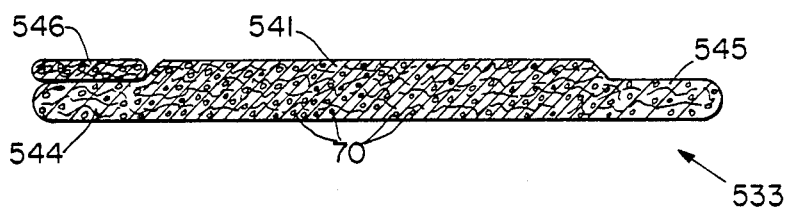
FIGS. 18, 19 and 20 are sectional views taken along sectional lines 18—18, 19—19 and 20—20, respectively, of FIG. 17.
Figure 19:
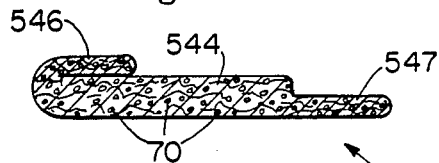
Figure 20:
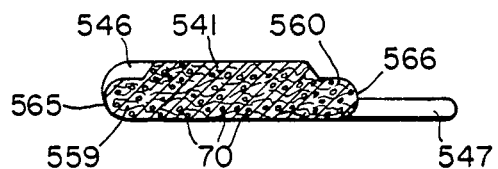
Figure 21:
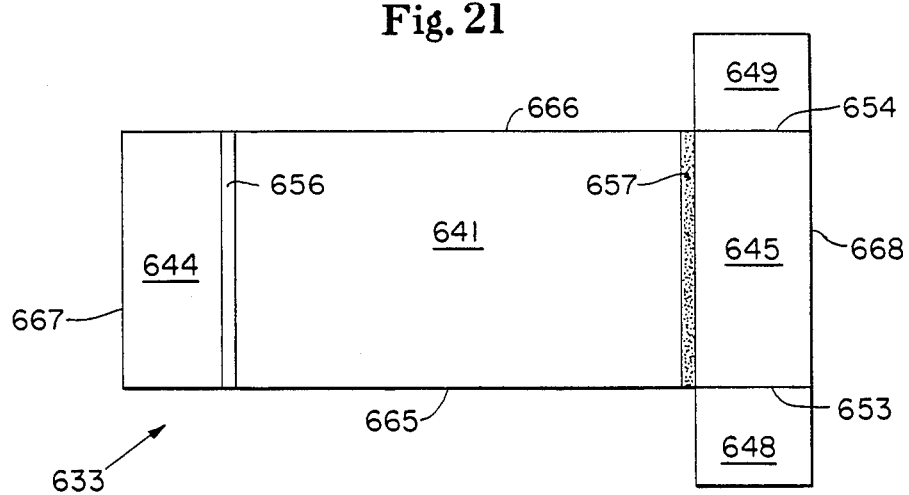
FIGS. 21 and 22 are plan view of T-shape absorbent cores constructed in accordance with the present invention: the FIG. 21 embodiment being generally rectilinear, and the FIG. 22 embodiment being somewhat curvalinear.
Figure 22:
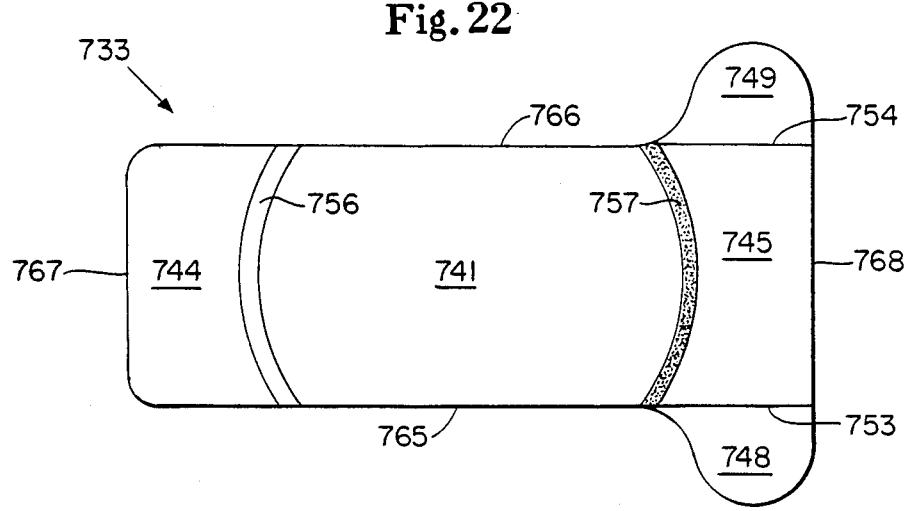

Absorbent cores 633 and 733, FIGS. 21 and 22, respectively, are T-shape cores which, but for not having ear regions on their front end portions are generally the equivalents of core 233, FIG. 11, and core 33, FIG. 1, respectively. Accordingly, further descriptions thereof are not included to avoid undue redundancy.

While particular embodiment of the present invention have been illustrated and described, it would be obvious to those skilled in the art that various other changes and modifications can be made without departing from the spirit and scope of the invention. In particular, while disposable diapers 30, 130 and 230, and absorbent cores 33, 133 and 233 thereof, respectively are shown to be somewhat hourglass shape, it is not intended to exclude rectangular or other shapes from the scope of the present invention. It is intended to cover in the appended claims all such changes and modifications that are within the scope of this invention.

What is claimed is:

1. A disposable diaper comprising a liquid pervious topsheet, a liquid impervious backsheet, and an absorbent core disposed intermediate said topsheet and said backsheet, said absorbent core comprising two longitudinally spaced end portions and a central portion disposed intermediate said end portions, said central portion having a greater average density and a greater average basis weight than said end portions, the ratio of the average density of said central portion to the average density of said end portions is about equal to or greater than 2:1.

2. The disposable diaper of claim 1 wherein the ratio of the density of said central portion to the density of said end portions is about equal to or greater than 2.5:1.

3. The disposable diaper of claim 1 wherein said absorbent core comprises a mixture of hydrophilic fibers and discrete particles of a highly absorbent particulate material having a fiber-to-particulate weight ratio of from about 70:30 to about 98:2.

4. The disposable diaper of claim 3 wherein only said central portion of said absorbent core comprises said mixture of hydrophilic fibers and discrete particulate material.

5. The disposable diaper of claim 3 or 4 wherein the range of said fiber-to-particulate weight ratio extends from about 75:25 to about 90:10.

6. A disposable diaper comprising a liquid pervious topsheet, a liquid impervious backsheet, and an absorbent core disposed intermediate said topsheet and said backsheet, said absorbent core comprising two longitudinally spaced end portions and a central portion disposed intermediate said end portions, said central portion having a greater average density and a greater average basis weight than said end portions, and said absorbent core comprises a mixture of hydrophilic fibers and discrete particles of a highly absorbent particulate material having a fiber-to-particulate weight ratio of from about 70:30 to about 98:2.

7. The disposable diaper of claim 6 wherein only said central portion of said absorbent core comprises said mixture of hydrophilic fibers and discrete particulate material.

8. The disposable diaper of claim 6 or 7 wherein the range of said fiber-to-particulate weight ratio extends from about 75:25 to about 90:10.

9. The disposable diaper of claim 1, 3 or 6 wherein said absorbent core additionally comprises at least one waistband assemblage having a medial region and a laterally spaced pair of ear regions, wherein at least one of said end portions is the medial region of said waistband assemblage of said core, and said ear regions and said medial region being complimentarily configured and disposed to enable folding said ear regions atop said medial region so that the lateral dimension of said folded waistband assemblage is about equal to or less than the width of said central portion of said core.

10. The disposable diaper of claim 9 wherein said waistband assemblage has substantially uniform density.

11. The disposable diaper of claim 9 wherein said ear regions are substantially thinner and more dense than said medial region of said waistband assemblage.

12. The disposable diaper of claim 1, 3 or 6 having a crotch region comprising said central portion and a pair of laterally spaced leg cuff portions which leg cuff portions extend laterally outwardly from the lateral side edges of said central portion, said leg cuff portions being of lesser average density and lesser average basis weight than said central portion, said leg cuff portions and said end portions being so configured and disposed that they corporately isolate said central portion from the edges of said core.

13. The disposable diaper of claim 12 wherein said end portions have lateral dimensions about equal to the composite width of said crotch region of said core, and wherein at least one of said end portions is the medial region of a waistband assemblage of said core, said waistband assemblage of said core further comprising a laterally spaced pair of ear regions, said ear regions and said medial region being complimentarily configured and disposed to enable folding said ear regions atop said medial region so that the lateral dimension of the folded waistband assemblage is about equal to or less than the width of said crotch region of said core.

14. The disposable diaper of claim 13 wherein said waistband assemblage has substantially uniform density.

15. The disposable diaper of claim 13 wherein said ear regions are substantially thinner and more dense than said medial region of said waistband assemblage.

16. The disposable diaper of claim 1, 3 or 6 wherein said portions are demarked from each other by sufficiently abrupt thickness differences that said core has a terraced character.

17. The disposable diaper of claim 1, 3 or 6 wherein said end portions have substantially greater resilience than said central portion.

18. The disposable diaper of claim 3 or 6 wherein said discrete particulate material and said fibers of said mixture are substantially uniformly dispersed with respect to each other.

19. The disposable diaper of claim 3 or 6 wherein said highly absorbent particulate material comprises hydrogel material that is substantially water-insoluble.

* * * * *

UNITED STATES PATENT AND TRADEMARK OFFICE
CERTIFICATE OF CORRECTION

PATENT NO.  : 4,685,915

DATED       : August 11, 1987

INVENTOR(S) : MARGARET H. HASSE et al.

It is certified that error appears in the above-identified patent and that said Letters Patent is hereby corrected as shown below:

| | |
|---|---|
| Column 6, Line 4, | "perform" should read ---preform---. |
| Column 6, Line 30, | "hydroxpropyl" should read ---hydroxypropyl---. |
| Column 6, Line 31, | "polyvinly" should read ---polyvinyl---. |
| Column 7, Line 14, | "an" should read ---and---. |
| Column 8, Line 8, | "curvalinear-shape" should read ---curvilinear-shape---. |
| Column 8, Line 32, | "embodiment" should read ---embodiments---. |

Signed and Sealed this

Sixteenth Day of February, 1988

Attest:

DONALD J. QUIGG

*Attesting Officer*    *Commissioner of Patents and Trademarks*